United States Patent
Nanjo

[11] Patent Number: 5,543,865
[45] Date of Patent: Aug. 6, 1996

[54] FUNDUS CAMERA WITH PARTIALLY COMMON COAXIAL OBSERVATION AND PHOTOGRAPHING OPTICAL SYSTEMS

[75] Inventor: Tsuguo Nanjo, Toyohashi, Japan

[73] Assignee: Nidek Co., Ltd., Japan

[21] Appl. No.: 373,020

[22] Filed: Jan. 17, 1995

[30] Foreign Application Priority Data

Feb. 2, 1994 [JP] Japan .................................... 6-031862

[51] Int. Cl.⁶ ..................................................... A01B 3/14
[52] U.S. Cl. ........................... 351/206; 351/221; 351/215
[58] Field of Search .................................... 351/206, 221, 351/215, 245

[56] References Cited

U.S. PATENT DOCUMENTS

| | | | |
|---|---|---|---|
| 5,048,946 | 9/1991 | Sklar et al. | 351/221 |
| 5,141,303 | 8/1992 | Yamamoto et al. | 351/221 |
| 5,240,006 | 8/1993 | Fujii et al. | 351/221 |
| 5,308,919 | 5/1994 | Minnich | 351/221 |
| 5,341,180 | 8/1994 | Isogai et al. | 351/206 |
| 5,475,451 | 12/1995 | Robert et al. | 351/221 |

*Primary Examiner*—William L. Sikes
*Assistant Examiner*—James A. Dudek
*Attorney, Agent, or Firm*—Rossi & Associates

[57] ABSTRACT

A fundus camera, which has an illumination optical system for illuminating a fundus of an examinee's eye, an observation optical system for observing the fundus and a photographing optical system for photographing an image of the fundus, the photographing system sharing partially a common optical path with the observation optical system, comprises a beam splitter disposed in the optical path of the photographing optical system, the optical path being used in common with the observation optical system, to dispose coaxially an optical path of the illumination optical system and same of the observation optical system and the photographing optical system, and photoelectric imaging elements disposed respectively in the observation optical system and the photographing optical system.

15 Claims, 3 Drawing Sheets

FUNDUS CAMERA WITH PARTIALLY COMMON COAXIAL OBSERVATION AND PHOTOGRAPHING OPTICAL SYSTEMS

BACKGROUND OF THE INVENTION

1. Field of the Invention

The present invention relates to a fundus camera which is capable of photographing of a fundus image, and more particularly to a fundus camera which is suitable for photographing of a fundus image of an eye of an examinee, particularly a man who lies on his back, babies and little children and animals and so on.

2. Description of Related Art

For an illumination optical system of so called a hand type fundus camera, conventionally, the following two kinds of methods have been proposed.

One is a separate illumination method wherein an illumination system and a photographing system are separately constructed, the illumination system having a small prism disposed slightly under a photographing optical path between an objective lens of the photographing system and an eye of an examinee, thereby illuminating the examinee's eye obliquely from under the eye.

Another is a coaxial illumination method wherein a semi-transparent mirror is disposed between an objective lens of a photographing system and an examinee's eye, so that a light beam of the illumination system and same of the photographing system are transmitted along optical paths being coaxial.

The former separate illumination method has the advantage of miniatuarizing an illumination system because the optical system thereof is simple and also may get the sufficient reflection light quantity from a fundus of the examinee's eye. On the other hand, preventing the prism of the illumination system from eclipsing a light beam of the photographing system and supplying illumination light to the fundus of the eye over the photographing visual field cause a demerit of a working distance coming to be very short. If the working distance between the examinee's eye and the apparatus comes to be short, it gives the examinee a dangerous feeling and an oppressive feeling, so that the examinee is apt to frequently blink his eyes and to move nervously his eyeball. Consequently, such motions often cause a bad influence on photographing of the fundus image of the eye.

Additionally, as the illumination system illuminates the examinee's eye from obliquely under the eye, upper and lower parts of a photographed picture are liable to often lack uniformity of illumination. When the pupil of the examinee's eye having a small diameter, illumination luminous flux is difficult to direct inside the eye, so that such an illumination system is not suitable for a photographing with no use of mydriatica, which utilizing natural mydriasis.

The latter illumination system has a merit of a longer working distance compared with the former separate illumination system, as well as a merit of not causing lack of uniformity of illumination. However, in this illumination system, large loss of light quantity is caused by the semitransparent mirror, which is then reduced to about a quarter of the light quantity. As a result, if the illumination system is used in fundus cameras which need sufficient light quantity for photographing, then a light source of illumination light must be remodeled to supply large quantity of light and to be large-sized.

SUMMARY OF THE INVENTION

The present invention has been made in view of the above circumstances and has an object to overcome the above problems and to provide a fundus camera which is compact and capable of retaining an enough working distance between an eye of an examinee and an apparatus.

Another object of the present invention is providing a compact and hand fundus camera which is capable of photographing a fundus image of the eye without using mydriatica.

The third object of the present invention is to provide a fundus camera enable confirmation whether photographed images are proper or not, and arrangement and storing of the photographed images.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, fundus camera of this invention comprising an illumination optical system for illuminating a fundus of an examinee's eye, an observation optical system for observing the fundus and a photographing optical system for photographing an image of the fundus, the photographing system sharing partially a common optical path with the observation optical system, the fundus camera comprises, a beam splitter disposed in the optical path of the photographing optical system, the optical path being used in common with the observation optical system, to dispose coaxially an optical path of the illumination optical system and same of the observation optical system and the photographing optical system, and photoelectric imaging elements disposed respectively in the observation optical system and the photographing optical system.

In the second aspect of the present invention, a fundus camera comprising a first illumination optical system for illuminating an eye of an examinee by infrared light, a second illumination optical system for illuminating the eye by visible light for photography, which shares a common optical path with the first illumination optical path, an observation optical system provided with a photoelectric imaging element having sensitivity to infrared light and a photographing optical system provided with a photoelectric imaging element having sensitivity to visible light area, which shares partially a common optical path with the observation optical system, and a beam splitter disposed in the common optical path of the photographing optical system and the observation optical system, to dispose coaxially an optical path of the first and second illumination optical systems with same of the observation-photographing optical system.

According to the present invention, it is possible to supply illumination light quantity necessary for photography without needing large-sized illumination system and to retain a sufficient working distance between the examinee's eye and the apparatus.

Further, the use of invisible illumination light in alignment can make photography without using mydriatica even with a compact fundus camera, so that the burden imposed on the examinee is largely lightened.

According to the present invention, a reduction of photographing light quantity can be achieved, damage to the examinee's eye by photographing light should be mitigated and the recovery time from the damage should be shortened accordingly.

As a photographed image can be displayed in an instant on a display, confirmation of quality of photography and retake of photography can effectively be conducted. It is accordingly possible to easily file and edit the photographed images.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.
In the drawings.

DETAILED DESCRIPTION OF THE PREFERRED EMBODIMENTS

A detailed description of one preferred embodiment of a fundus camera embodying the present invention will now be given referring to the accompanying drawings.

Figure 1:
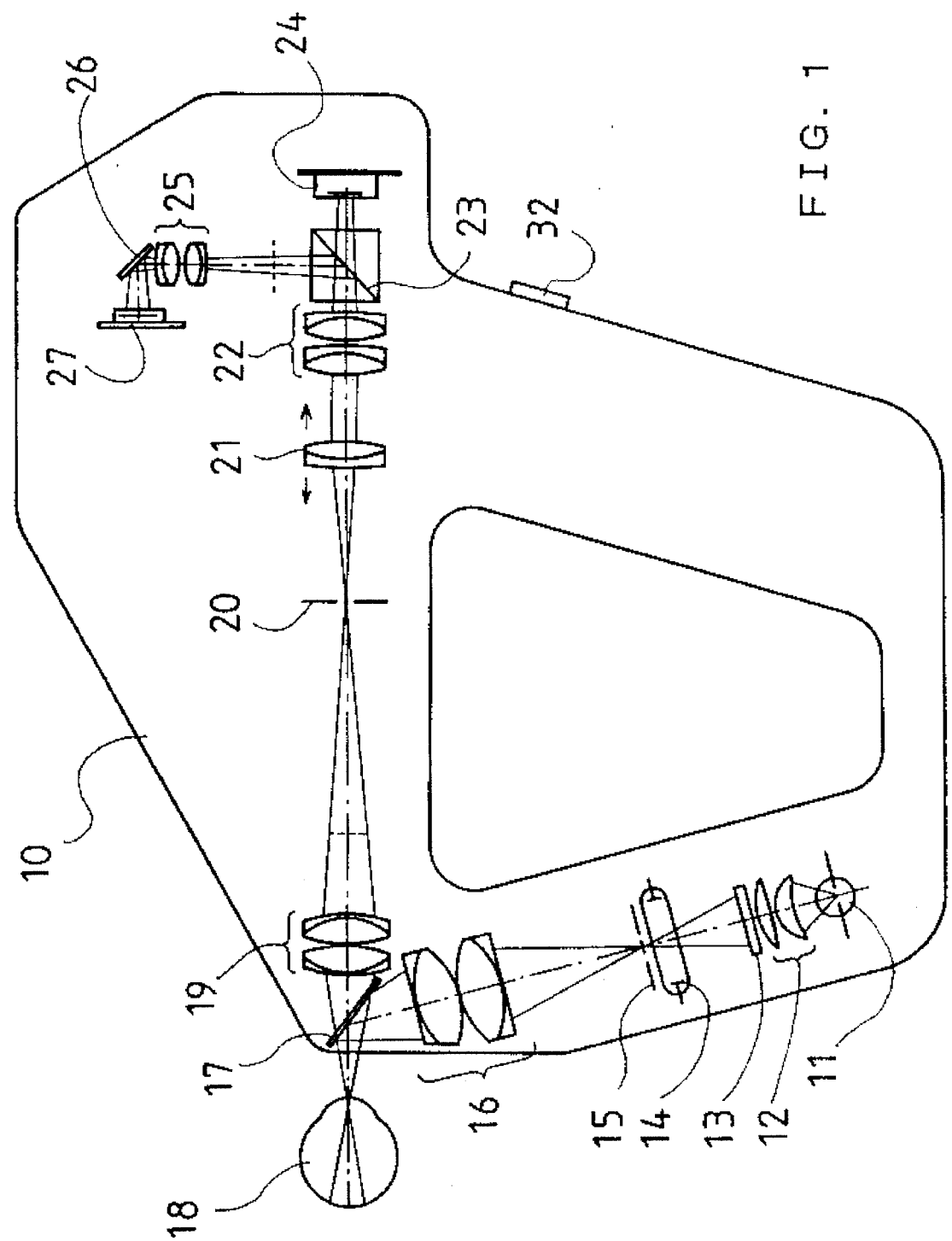
FIG. 1 is a schematic side view of an optical system of an apparatus in the first embodiment according to the present invention.

FIG. 1 shows a schematic side view of an optical system of the fundus camera in the present embodiment. The optical system is constructed of an illumination optical system and an observing-photographing optical system, which are disposed in a body 10. This body 10 refers to common body forms on the markets, one of the forms being illustrated in FIG. 1.

(Illumination Optical System)

The illumination optical system has a halogen lamp 11 which is a light source of observing illumination light, a condenser lens 12, an infrared filter 13, a flash lamp 14 which is a light source of photographing light, a ring slit 15 which is a ring formed aperture diaphragm, relay lenses 16 and a beam splitter 17 which reflects illumination light to direct into an eye 18 of an examinee along the same optical path as that of photographing light. The infrared filter 13 serves to shut out light of visible wavelength area thereby to limit observing illumination light to invisible light.

Luminous flux emitted from the halogen lamp 11 is condensed through the condenser lens 12 and only invisible light is allowed to pass through the infrared filter 13. Then, the luminous flux passed through the infrared filter 13 is projected onto the ring slit 15 and is thereby formed a ring-shaped light beam. The ring-shaped luminous flux is transmitted through the relay lenses 16 and reflected by the beam splitter 17, then the light quantity of the luminous flux is attenuated to about a half. The luminous flux reflected by the beam splitter 17 is directed to the eye 18 and forms an image of the ring slit 15 on near the pupil of the eye 18. The size of the image of the ring slit 15 formed on near the pupil is reduced to an outer diameter which corresponds to a small pupil of about 4 mm in diameter that is needed for non-mydriasis photography. After formed the ring slit image, the illumination luminous flux is diffused to illuminate a fundus over a visual field to be photographed or slightly wider than the visual field.

(Observing-Photographing Optical System)

The observing-photographing optical system has an objective lens 19, a photographing diaphragm 20, a focusing lens 21, an image forming lens 22, a dichroic mirror 23 which reflects infrared light and allows mostly visible light to pass therethrough, an imaging element 24 of a CCD camera, relay lenses 25 to elongate an optical path, a mirror 26 to turn a reversed mirror image back and an imaging element 27 of an infrared CCD camera for observation. The photographing diaphragm 20 is disposed in a substantially conjugate relationship with respect to a pupil of an examinee's eye 18 through the objective lens 19. The focusing lens 21 is movable along an optical path by a lens moving device to adjust according to the refractive power of an examinee's eye. The imaging element 24 has, even in color photography, sensitivity of 10 times or more as compared with in photography with a 35 mm film of ASA 100, the light quantity of the flash lamp 14 may be reduced accordingly.

The reflection luminous-flux from the fundus of the eye 18 while being illuminated by the illumination optical system is once condensed at a center point of an optical axis of the eye 18, which is a non-overlapping position with respect to the image of the ring slit 15. The luminous flux condensed is further attenuated to about a half light quantity by the beam splitter 17 and then converged to a photographing diaphragm 20 by the objective lens 19. As the photographing diaphragm 20 is disposed in a conjugate relationship with respect to the pupil of the eye 18, the diameter of photographing luminous flux which returns from the pupil of the eye 18 is determined by the photographing diaphragm 20 so that the photographing luminous flux does not overlap with the image of the ring slit 15 of the illumination optical system.

The infrared luminous flux passed through the photographing diaphragm 20 is transmitted through the focusing lens 21 and the image forming lenses 22, and reflected by the dichroic mirror 23 toward the relay lenses 25. The infrared luminous flux passed through the relay lenses 25 is reflected by the mirror 26 and projected onto the imaging element 27 to form a fundus image thereon. The fundus image is then displayed on a monitor display 31 mentioned later.

The visible luminous flux is transmitted through the focusing lens 21, the image forming lenses 22 and the dichroic mirror 23, then projected onto the imaging element 24 of a CCD camera to form a fundus image thereon. The photographed image of the fundus is displayed as a stationary picture on a color monitor display 41 mentioned later.

The imaging element 24 of the photographing CCD camera and the imaging element 27 of the infrared CCD camera may be changed the position with each other by replacing the dichroic mirror 23 with a cold mirror which reflects visible light and allows infrared light to pass therethrough. It is also possible to use a quick return mirror instead of the dichroic mirror.

Operation of the apparatus constructed above will be described hereinafter referring to FIG. 2 which shows a whole construction of the apparatus and FIG. 3 which shows a block diagram of an electric system.

Figure 2:
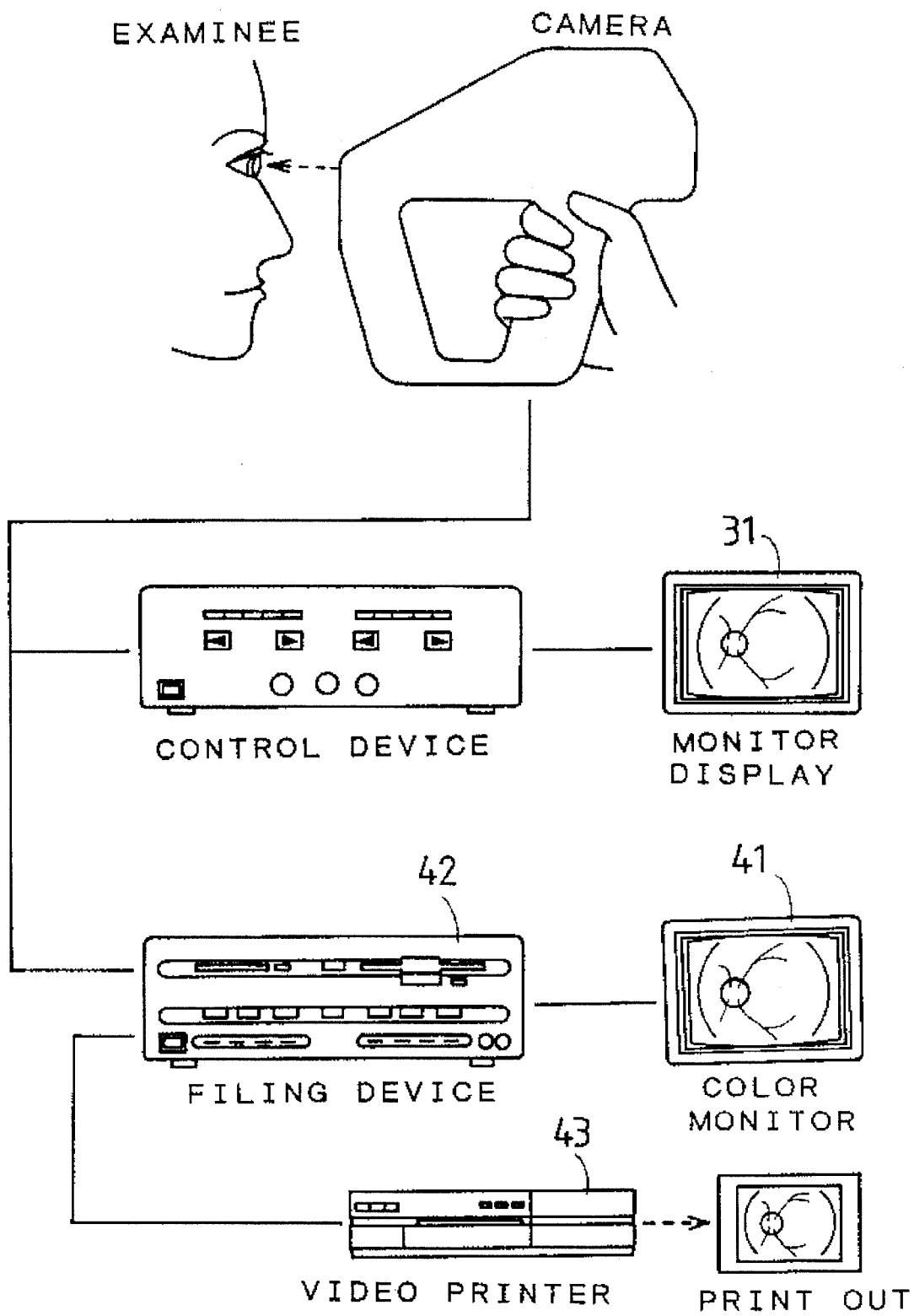
FIG. 2 is a schematic view showing a whole construction of the apparatus in the first embodiment.
Figure 3:
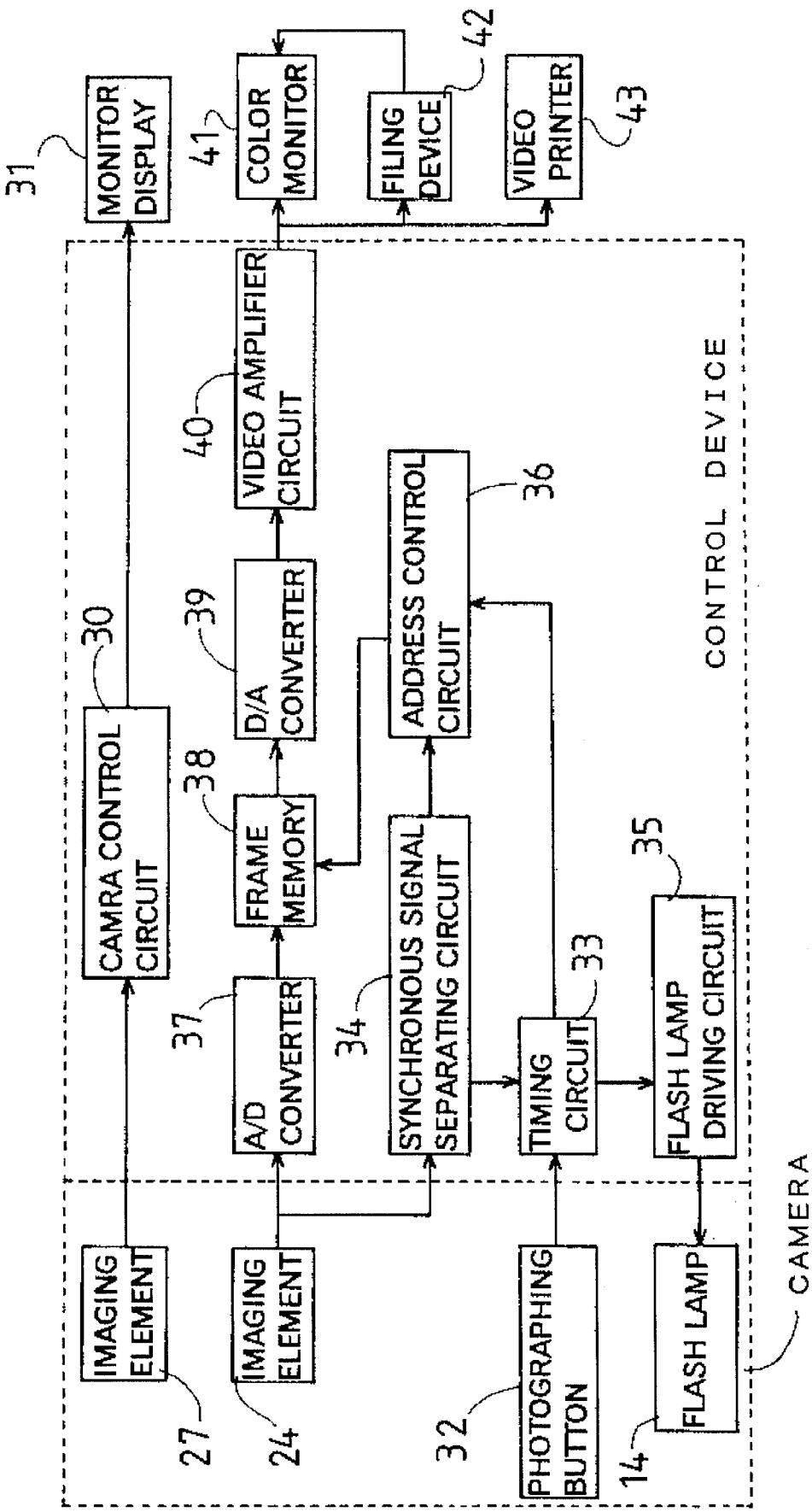
FIG. 3 is a block diagram of an electrical system of the apparatus in the first embodiment.

As shown in FIG. 2, the apparatus is as a whole constituted of a camera, a control device, a monitor display device, a color monitor device, a filing device and a video printer. A suitable photographing environment is a place at the light level that characters in newspapers can barely be read and a pupil of an examinee's eye will open widely due to natural mydriasis. A photographer turns on the halogen lamp 11 while holding the body 10 internally having optical systems in one hand, and brings the body 10 from slightly this side of the examinee's eye close to the eye to illuminate same. Illumination luminous flux is limited to invisible light by the infrared filter 13, so that the eye is illuminated without causing miosis. Reflection luminous flux from the eye while being illuminated by the infrared luminous flux is detected at the imaging element 27 of the infrared CCD camera, and the photographed image is then displayed on the monitor display 31 through the camera control circuit 30. As the fundus image of the examinee's eye to be displayed on the monitor display 31, the image of the anterior part of the eye is first displayed because the apparatus illuminates at the start the eye from slightly this side. While observing the image first displayed, the photographer brings the apparatus near a proper position of a working distance thereof. Accordingly, image of the pupil is then displayed on the monitor display 31 and then an image of the fundus comes to be displayed thereon.

Next, the photographer adjusts the apparatus in up and down, right and left directions in accordance with an alignment index not shown. When the image of the fundus is dim due to the refractive power of the eye, the focusing lens 21 is moved so as to focus the fundus. Such a focusing operation on the fundus may use a conventional focusing index and the like, for example, a split bright base line. Fine alignment is further conducted to determine a visual field.

When focusing and determining of the visual field on the fundus are achieved, a photographing button 32 is depressed. By depression of the button 32, a trigger signal is generated and input into a timing circuit 33. The timing circuit 33 transmits the trigger signal to a flash lamp driving circuit 35 and an address control circuit 36 respectively in synchronous with a synchronous signal of the imaging element 24, which is input via a synchronous signal separating circuit 34 into the timing circuit 33. The flash lamp driving circuit 35 accordingly drives the flash lamp 14 to emit light. The image of the fundus is detected at the imaging element 24. The video image signal detected at the imaging element 24 is converted into a digital signal at an A/D converter 37 and is stored in a frame memory 38 in synchronous with the signal from the address control circuit 36.

The photographed image stored in the frame memory 38 is converted into an analog signal at a D/A converter 39, transmitted to a color monitor display 41 via a video amplifier circuit 40 and in an instant displayed on the color monitor display 41. The photographer confirms whether the image of the fundus being displayed on the color monitor display 41 is well photographed. If the photographed image is not proper, the same photographing operation will be started over again.

If storing of the photographed image is requested, video image data thereof are stored through operation of a filing device 42. The video image data of the fundus being stored in the filing device 42 may be allowed to reproduce, while unnecessary video image data are deleted thereby to edit data. If printed picture images are required for the purpose in attaching on a clinical record card and the like, a video printer 43 is operated to print out them.

The monitor display 31 may be disposed separately from the imaging elements and so on, more preferably, the use of a compact liquid crystal display and the like as the monitor display 31 and setting of the imaging elements and the display in a body may improve better operations with the apparatus.

The present invention may be embodied in other specific forms without departing from the spirit or essential characteristics thereof. For instance, two monitor display devices; a monitor display 31 and a color monitor display 41, are used in the above embodiment, it is possible to use only the color monitor display 41 if picture changing means is additionally provided and observing picture images and photographing video images may alternatively be displayed on the monitor 41.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A fundus camera comprising an illumination optical system for illuminating a fundus of an examinee's eye, an observation optical system for observing the fundus and a photographing optical system for photographing an image of the fundus, the photographing system sharing partially a common optical path with the observation optical system, the fundus camera comprising:

a beam splitter disposed in the common optical path to dispose coaxially an illuminating optical path of said illumination optical system and said common optical path; and photoelectric imaging elements disposed respectively in said observation optical system and said photographing optical system.

2. A fundus camera according to claim 1, further comprising a hand body.

3. A fundus camera according to claim 2, further comprising a mirror which selects wavelength of light, through which the optical path of said observation optical system and same of said photographing optical system are divided.

4. A fundus camera according to claim 3, further comprising a hand body.

5. A fundus camera according to claim 1, wherein said illumination optical system comprises a first illumination optical system for illuminating the examinee's eye by infrared light and a second illumination optical system for illuminating the eye by visible light for photography, which shares partially a common optical path with said first illumination optical system, the photoelectric imaging element of said observation optical system has sensitivity to infrared light area while same of the photographing optical system has sensitivity to visible light area.

6. A fundus camera according to claim 5, further comprising a hand body.

7. A fundus camera as claimed in claim 1, wherein said observation optical system comprises an infrared observing light.

8. A fundus camera comprising an illumination optical system for illuminating a fundus of an examinee's eye, an observation optical system for observing the fundus and a photographing optical system for photographing an image of the fundus, the photographing system sharing partially a common optical path with the observation optical system, the fundus camera comprising:

a beam splitter disposed in the optical path of said photographing optical system, the optical path being used in common with the observation optical system, to dispose coaxially an optical path of said illumination optical system and same of said observation optical system and said photographing optical system;

photoelectric imaging elements disposed respectively in said observation optical system and said photographing optical system; and a ring shaped aperture diaphragm disposed in a common optical path of said observation and photographing optical systems and at a position being in a substantially conjugate relationship with a pupil of the examine's eye, the aperture diaphragm serving to form a ring image having a size of about 4 mm at a position of the pupil.

9. A fundus camera according to claim 8, further comprising a hand body.

10. A fundus camera comprising:

a first illumination optical system for illuminating an eye of an examinee by infrared light;

a second illumination optical system for illuminating the eye by visible light for photography, which shares a first common optical path with said first illumination optical system;

an observation optical system provided with a photoelectric imaging element having sensitivity to infrared light and a photographing optical system provided with a photoelectric imaging element having sensitivity to visible light area, which share, partially, a second common optical path; and a beam splitter disposed in the second common optical path, to dispose coaxially the second common optical path and said first common optical path.

11. A fundus camera according to claim 10, further comprising a filing apparatus to store and retain an image of the fundus detected by the photoelectric imaging element of said photographing optical system.

12. A fundus camera comprising:

an illuminating optical system for illuminating a fundus of an examinee's eye, an observation optical system for observing the fundus, and a photographing optical system for photographing an image of the fundus;

said observing and photographing optical systems sharing, partially, a common optical path and meeting an illuminating optical path of said illuminating optical system at a predetermined angle;

a beam splitter disposed in the common and illuminating optical paths such that said illuminating optical path is reflected off a first face of said beam splitter to the examinee's eye and such that said common optical path passes through said first face and a second face of the beam splitter whereby said illuminating and common optical paths are disposed coaxially from the first face of the beam splitter to the examinee's eye; and photoelectric imaging elements disposed respectively in said observation and photographing optical systems.

13. A fundus camera as claimed in claim 12, wherein said observation optical system comprises an infrared observing light.

14. A fundus camera comprising an illumination optical system for illuminating a fundus of an examinee's eye, an observation optical system for observing the fundus and a photographing optical system for photographing an image of the fundus, the photographing system sharing partially a common optical path with the observation optical system, the fundus camera comprising:

a beam splitter, positioned such that an illuminating optical path of said illumination optical system reflects off of a first face of said beam splitter and such that said common optical path passes through said first face and a second face of said beam splitter, said beam splitter further disposed in the common optical path to dispose coaxially said illuminating optical path of said illumination optical system and said common optical path; and photoelectric imaging elements disposed respectively in said observation optical system and said photographing optical system.

15. A fundus camera comprising:

a first illumination optical system for illuminating an eye of an examinee by infrared light;

a second illumination optical system for illuminating the eye by visible light for photography, which shares a first common optical path with said first illumination optical system;

an observation optical system provided with a photoelectric imaging element having sensitivity to infrared light and a photographing optical system provided with a photoelectric imaging element having sensitivity to visible light area, which share, partially, a second common optical path; and a beam splitter positioned such that said first common optical path of said first and second illumination optical systems reflects off of a first face of said beam splitter and such that said second common optical path of said observation and photographing optical systems passes through said first face and a second face of said beam splitter, said beam splitter further disposed in the second common optical path, to dispose coaxially the second common optical path and said first common optical path.

* * * * *